United States Patent
Reichmuth et al.

(10) Patent No.: US 9,579,645 B2
(45) Date of Patent: Feb. 28, 2017

(54) FLUID TRANSFER APPARATUS

(71) Applicant: Eppendorf AG, Hamburg (DE)

(72) Inventors: Burkhardt Reichmuth, Hamburg (DE); Herbert Belgardt, Hamburg (DE); Stefen Hofmann, Hamburg (DE); Mike Queck, Hamburg (DE)

(73) Assignee: Eppendorf AG, Hamburg (DE)

( * ) Notice: Subject to any disclaimer, the term of this patent is extended or adjusted under 35 U.S.C. 154(b) by 230 days.

(21) Appl. No.: 14/356,843

(22) PCT Filed: Nov. 6, 2012

(86) PCT No.: PCT/EP2012/004622
§ 371 (c)(1),
(2) Date: May 7, 2014

(87) PCT Pub. No.: WO2013/068099
PCT Pub. Date: May 16, 2013

(65) Prior Publication Data
US 2014/0308750 A1    Oct. 16, 2014

Related U.S. Application Data

(60) Provisional application No. 61/556,314, filed on Nov. 7, 2011.

(30) Foreign Application Priority Data

Nov. 7, 2011    (DE) .................. 10 2011 117 963

(51) Int. Cl.
*B01L 3/02* (2006.01)
*G01F 25/00* (2006.01)
(Continued)

(52) U.S. Cl.
CPC ............. *B01L 3/0237* (2013.01); *B01L 3/021* (2013.01); *B01L 3/0217* (2013.01); *B01L 3/0234* (2013.01);
(Continued)

(58) Field of Classification Search
CPC ............. B01L 2300/0636; B01L 3/021; B01L 3/0237; Y10T 436/2575
See application file for complete search history.

(56) References Cited

U.S. PATENT DOCUMENTS

2002/0005075 A1    1/2002   Kriz
2002/0018734 A1*   2/2002   Braun .................. B01L 3/0234
                                                                 422/518
(Continued)

FOREIGN PATENT DOCUMENTS

JP    A-2002181839       6/2002
WO    WO 2012045415 A1   4/2012

*Primary Examiner* — Jennifer Wecker
(74) *Attorney, Agent, or Firm* — Todd A. Lorenz

(57) ABSTRACT

The invention relates to a fluid transfer apparatus, in particular pipetting apparatus, for transferring at least one fluid laboratory sample, in particular a biochemical or medical laboratory sample, comprising a base body, which has a connecting section serving for connecting a container to the base body for the intake of the at least one fluid sample into the container, a movement device, which can bring about the intake and/or delivery of at least one fluid laboratory sample into the container, an electrical control device, which controls at least one function of the fluid transfer apparatus, a sensor device, which comprises at least one acceleration sensor which is signal-connected to the control device and by means of which at least one acceleration value can be measured during the movement of the fluid transfer apparatus, wherein the control device is designed such that it uses the at least one acceleration value during the control of the (Continued)

at least one function. The invention furthermore relates to a method for using at least one acceleration value in a fluid transfer apparatus.

3 Claims, 2 Drawing Sheets

(51) Int. Cl.
    *G01N 1/14* (2006.01)
    *G01N 9/34* (2006.01)
    *G01N 35/10* (2006.01)
    *B01L 3/00* (2006.01)

(52) U.S. Cl.
    CPC ........... *B01L 3/0275* (2013.01); *B01L 3/0279* (2013.01); *B01L 3/502* (2013.01); *B01L 2200/143* (2013.01); *B01L 2300/0627* (2013.01); *B01L 2300/0636* (2013.01); *G01N 1/14* (2013.01); *G01N 35/10* (2013.01); *G01N 35/1016* (2013.01); *Y10T 436/2575* (2015.01)

(56) References Cited

U.S. PATENT DOCUMENTS

| | | | |
|---|---|---|---|
| 2002/0177237 A1* | 11/2002 | Shvets | B01L 3/0265 436/180 |
| 2005/0118069 A1* | 6/2005 | Solotareff | B01L 3/0217 422/400 |
| 2007/0203457 A1* | 8/2007 | Kohn | B01L 3/0234 604/187 |
| 2007/0211566 A1* | 9/2007 | Ebers | G01F 11/0008 366/208 |
| 2008/0210023 A1 | 9/2008 | Telimaa et al. | |
| 2009/0000350 A1* | 1/2009 | Magnussen | B01L 3/0217 73/1.74 |
| 2010/0004772 A1* | 1/2010 | Elfstrom | G06Q 10/06 700/103 |
| 2010/0199789 A1 | 8/2010 | Magnussen et al. | |
| 2011/0277532 A1* | 11/2011 | Bartholomeyczik | G01P 21/00 73/1.38 |
| 2013/0089656 A1* | 4/2013 | McComiskey | C23C 24/08 427/8 |

* cited by examiner

FLUID TRANSFER APPARATUS

The invention relates to a fluid transfer apparatus, in particular a pipetting apparatus, and to a method for using it.

Such fluid transfer apparatuses are primarily used in a laboratory for transporting fluid samples, in particular for metering the samples. In the case of pipetting apparatuses, e.g. liquid samples are sucked by means of reduced pressure into pipette tips, stored there, and ejected therefrom again at the target site.

The fluid transfer apparatuses include metering apparatuses, in particular pipetting apparatuses, in particular handheld pipetting apparatuses, such as e.g. pipettes and dispensers. A pipette is understood to mean an instrument in which, by means of a movement device which is assigned to the instrument and which can comprise a piston, in particular, a volume to be pipetted can be sucked into a pitetting container connected to the pipette. A dispenser is understood to mean an instrument in which, by means of a movement device which can comprise a piston, in particular, a volume to be pipetted can be sucked into a pipetting container connected to the dispenser, wherein the movement device is at least partly assigned to the pipetting container, e.g. by the piston being arranged in the pipetting container. In the case of a handheld pipetting apparatus, the sample quantity delivered by an individual actuation can correspond to the sample quantity sucked into the instrument. However, provision can also be made for a sample quantity that has been taken in and corresponds to a plurality of delivery quantities to be delivered again in steps. Moreover, a distinction is made between single-channel instruments and multi-channel instruments, wherein single-channel instruments contain only a single delivery channel and multi-channel instruments contain a plurality of delivery channels which, in particular, allow the parallel delivery or intake of a plurality of sample volumes. Pipetting apparatuses can be manually operated, in particular, i.e. imply user-generated driving of the movement device, and can be electronically operated, in particular.

Examples of manually operated pipettes are the Eppendorf Reference® and the Eppendorf Research® from Eppendorf AG, Hamburg, Germany; one example of a manually operated dispenser is the Multiplette® plus from Eppendorf AG; one example of an electronic pipette is the Eppendorf Xplorer® from Eppendorf AG; examples of electronic dispensers are the Multipette stream® and Xstream® from Eppendorf AG.

Such fluid transfer apparatuses are used in laboratories in order to meter and transport, in particular, extremely small sample quantities in the range of a few tenths of a microliter to milliliters with extremely high precision. It is often of importance to analyse biochemical or medical samples which represent a considerable value, e.g. by virtue of the fact that they can only be produced with high outlay or, as in the case of forensic samples, can only be obtained with very great difficulty. In these cases it is important to carry out the processing of the samples with the highest possible precision that remains as constant as possible. For this purpose, firstly the reliability of the apparatus and secondly the ergonomics when using the apparatus are of importance.

Particularly in the case of manually operated fluid transfer apparatuses, the continual or repeated manual mechanical actuation of the apparatus makes demands both on the apparatus and on the user and thus influences firstly the ageing process and wear of the instrument and secondly the operating convenience for the user. This holds true when the fluid transfer apparatus is actuated intensively as part of an e.g. automated system. It would therefore be desirable to reduce the intensity of the actuation of the fluid transfer apparatus with productivity remaining the same in order to improve the operating convenience and to maintain the reliability of the instrument, or in particular to obtain at least information about the intensity of the actuation in order to be able to estimate the reliability when using the fluid transfer apparatus.

Taking this as a departure point, the invention is based on the object of providing an improved fluid transfer apparatus which makes possible, in particular, convenient and permanently reliable operation of the fluid transfer apparatus.

The object is achieved by means of the fluid transfer apparatus described herein. The dependent claims relate to preferred configurations.

The fluid transfer apparatus according to the invention, in particular pipetting apparatus, for transporting or transferring at least one fluid laboratory sample, in particular a biochemical or medical laboratory sample, comprises: a base body which has a connecting section serving for connecting a container to the base body for the intake of the at least one fluid sample, a movement device, which can bring about the intake and/or delivery of at least one fluid laboratory sample into the container, an electrical control device, which controls at least one function of the fluid transfer apparatus, a sensor device, which comprises at least one acceleration sensor which is signal-connected to the control device and by means of which at least one acceleration value can be measured during the movement of the fluid transfer apparatus, wherein the control device is designed such that it uses the at least one acceleration value during the control of the at least one function.

The fluid transfer apparatus according to the invention affords the advantage that changes in the movement state of the fluid transfer apparatus can be automatically detected and used and, in particular, utilized for carrying out, in particular, the function automatically in a manner dependent on the acceleration value. The operating convenience increases as a result. Changes in the movement state which can occur, for example, upon mechanical loading or actuation of the fluid transfer apparatus and adversely affect the reliability of the fluid transfer apparatus can be detected and evaluated. The function can be a test function that uses, in particular observes and in particular also evaluates, the at least one acceleration value, in particular in order to characterize the mechanical loading of the fluid transfer apparatus. Extreme loading values can be determined or loading values can be summed in order to obtain summed loading values as a measure of the continuous loading of the fluid transfer apparatus. The loading values determined can make it possible for the user of the fluid transfer apparatus to draw conclusions about the reliability thereof. With regard to the use of the acceleration value for influencing a function of the fluid transfer apparatus, various preferred configurations are described below.

A fluid transfer apparatus is understood according to the invention to be an apparatus by means of which a fluid can be transferred into a container for the fluid, and in particular can be delivered from there again. The fluid transfer apparatus can be a metering apparatus designed for metering a fluid to be transferred and/or can be, in particular, a pipetting apparatus. In the case of a pipetting apparatuses, a fluid is sucked into the container by means of a reduced pressure. The reduced pressure is preferably generated by a piston of a movement device, said piston being movable in a cylinder. The piston is moved, in particularly manually or mechanically, in particular by an electric drive. The reduced pressure can be generated with the aid of an expandable air volume between fluid and fluid-side piston end. As an alternative thereto, in the direct displacer principle, the fluid-side piston end is brought into direct contact with the fluid or brought at least into direct proximity to the fluid.

The pipetting apparatus is preferably a pipette or a dispenser. The pipetting apparatus can furthermore be manually operated or electrically operated and for this purpose have, in particular, a manually operated or an electrically operated movement device. A pipetting apparatus can be a single-channel instrument or a multi-channel instrument.

The fluid transfer apparatus is preferably a movable or acceleratable apparatus, in particular a mechanically movable apparatus or a handheld apparatus. For this purpose, it preferably comprises a handheld section. Preferably, the base body is designed as a handle section or comprises a handle section which is gripped by the user's hand in order to hold, and in particular to move and operate, the fluid transfer apparatus. Preferably, the fluid transfer apparatus is designed for single-handed operation, such that all processes required for fluid transfer can be implemented with one hand. However, the fluid transfer apparatus can also be part of a laboratory apparatus, e.g. of an automatic laboratory machine.

The base body preferably comprises a housing, in which the movement device can be at least partly or completely arranged. Preferably, the control device is at least partly or completely arranged in the base body.

The movement device serves for moving the fluid for the transfer thereof and serves, in particular, for the intake of the fluid into the container and delivery of the fluid from the container. In the case of a manually operating movement device, the latter preferably comprises an actuation element, in particular an operating button, for the actuation of which the user applies the force for moving the fluid, e.g. by tensioning a spring. In the case of an electrically operated movement device, the force for moving the movement device is applied by means of an electrical drive, which can use, in particular, a battery or a rechargeable battery, which can in each case be part of the fluid transfer apparatus, in particular of the base body. The movement device preferably comprises a piston device having a piston that is movable in a cylinder of the piston device in order to generate a reduced pressure in said cylinder. However, the movement device can also be designed to move a piston that is only partly or not at all part of the fluid transfer apparatus, as in the case e.g. when moving the piston of a syringe container.

The pipetting apparatus is preferably designed for the transfer, in particular metering, of small quantities of fluid. The latter are understood to mean, in particular, fluid volumes in the range of between 0.1 µl and 200 ml. Said fluids are usually aqueous liquids but can e.g. also be other inorganic or organic liquids. The metering accuracy, preferably measured according to EN ISO 8655, for the systematic measurement error (SMA) is respectively preferably SMA=+/−(0.02-0.08) µl given an aqueous fluid volume V=1 µl, SMA=+/−(0.08-0.16) given V=10 µl, SMA=+/−(0.6-1.0) µl given V=100 µl. The relative systematic measurement error (SMA/V) is preferably between 5-50 per mille. The systematic measurement error is the deviation of the metered volume from the nominal volume or from the chosen volume of the pipetting apparatus. It can be determined by averaging from ten measurements.

A container that can be connected to the connecting section of the fluid transfer apparatus is preferably designed for the intake of the small fluid volume. Said container can be a pipette tip or a dispenser tip, which, in particular, can in each case comprise a movable piston. In the latter case, the container is fashioned according to the syringe principle, in particular, and is designated as a syringe container. Containers are preferably composed of plastic and are preferably consumables, that is to say after single use they are preferably not cleaned but rather disposed of. However, they can also be composed of other materials and in particular reusable, in particular autoclavable in a biological or medical laboratory.

The sensor device preferably comprises at least one acceleration sensor, preferably exactly one acceleration sensor. Acceleration sensors are commercially available and are based on different measurement principles in a known manner. Said principles are based e.g. on piezoresistivity, piezoelectric effect, use of the Hall effect, thermal effects or the resonance of quartz oscillators. A capacitive semiconductor sensor is preferably used as acceleration sensor since such semiconductor sensors can be made very small and produced cost-effectively in the context of micromechanics and their measurements are substantially independent of temperature, in contrast to other types of acceleration sensor. Suitable types of acceleration sensor are e.g. MEMS sensors (MEMS: micro-optoelectro-mechanical systems). An acceleration sensor can also comprise electrical circuits, e.g. integrated circuitry, for evaluating the measured acceleration values. Suitable commercial acceleration sensors are obtainable e.g. from the manufacturer STMICROELECTRONICS, Geneva, Switzerland.

The acceleration sensor preferably has at least one measurement range comprising minimum and maximum detectable acceleration values of between preferably (+/−) 0.5 to 10 g, preferably (+/−) 0.5 to 2 g. 1 g corresponds, in particular, to the acceleration due to gravity and can be fixed at 9.8 m/(s*s). The acceleration sensor preferably has a resolution of measurement in the range of 1.0 mg to 32.0 mg, preferably between 5.0 mg and 20.0 mg.

The measurement of 1 g, preferably, corresponds to the gravity, which in this case can act as the only force on the acceleration sensor. Therefore, a measured quantity of 1 g can correspond to the gravity, which acts on an otherwise unaccelerated sensor. Moreover, it is possible that a negative value of the acceleration of the sensor in a direction corresponds to a deceleration of the sensor in said direction. Preferably, the acceleration sensor is designed to measure the acceleration in at least one spatial direction or preferably in all three orthogonal spatial directions. Preferably, the control device is designed to use and/or evaluate the at least one acceleration value corresponding to the measurement in a spatial direction. Preferably, the control device is designed to use and/or evaluate the plurality of acceleration values corresponding to the measurements in at least two spatial directions, or corresponding to exactly three, in particular orthogonal, spatial directions, or corresponding to the total of 6 spatial directions resulting from the positive and negative directions of the three orthogonal spatial axes. In this way, the control device can evaluate the acceleration and thus, in particular, the loading in an even more detailed and more reliable manner.

Moreover, an acceleration value can be derived using the results of the measurement in at least one spatial direction, or parallel to said direction. In particular, an acceleration value can be derived using the results of the measurement in two, preferably orthogonal, spatial directions, or parallel to said directions. Moreover, an acceleration value can be derived using the results of the measurement in three, preferably orthogonal, spatial directions, or parallel to said directions. Such an acceleration value can be the sum of at least two, in particular two or three acceleration values, which have been measured in at least two, preferably two or three, preferably orthogonal, spatial directions, or parallel to said directions. In general, a "value" can mean the "absolute value".

Preferably, the fluid transfer apparatus comprises at least one operating element serving, in particular, for inputting and/or outputting information between the user and the control device. The operating element can comprise at least one operating button or keyboard, at least one display or touch screen. The fluid transfer apparatus can also comprise means for outputting acoustic indications, e.g. a loudspeaker.

The electrical control device preferably comprises at least one printed circuit board and preferably components having integrated circuits (ICs), which are preferably arranged on at least one printed circuit board. Preferably, the control device comprises programmable electrical circuits. Preferably, the sensor device, in particular the at least one acceleration sensor, is also arranged on the printed circuit board, which makes possible a particularly simple, compact and/or power-saving design.

The control device preferably comprises a signal processing device, by means of which the at least one acceleration value is detected and used for controlling a function of the fluid transfer apparatus. The signal processing device can be part of the evaluation device or form the latter. The acceleration value can be present either as an analogue signal, e.g. electrical voltage signal, or as a digital value. The signal processing device is preferably designed for processing analogue signals, which is designated as an analogue signal processing device, by means of which, in particular, the at least one acceleration value is detected as an analogue signal and is used for controlling a function of the fluid transfer apparatus, in particular is evaluated in an analogue fashion. Preferably, the signal processing device comprises a digital data processing device comprising, in particular, a computing unit (CPU), databuses, data memories, a microprocessor, one or more interfaces for apparatus-internal or -external data transfer, and/or one or more signal connections, e.g. line-conducted or wireless, to other electrical devices. Preferably, the control device is designed to digitally detect, in particular digitally process, in particular digitally evaluate and in particular digitally store, the at least one acceleration value.

Preferably, the control device comprises an acceleration value memory, in particular acceleration data memory, for storing the at least one acceleration value or a multiplicity of acceleration values measured temporally successively or at least partly simultaneously. Different configurations of the fluid transfer apparatus according to the invention can thereby be realized. Preferably, the control device comprises a time detecting device, by means of which information about relative or absolute points in time is available. Preferably, the absolute time can be corrected and set, e.g. by the user. The time detecting device can also be part of the sensor device, in particular part of an acceleration sensor. Further configurations of the fluid transfer apparatus according to the invention can be realized by the time detecting device. Preferably, the control device comprises a time data memory for storing the at least one acceleration value or a multiplicity of acceleration values measured temporally successively. The acceleration data memory and the time data memory are preferably accommodated in the same physically rewritable memory component, e.g. RAM, FLASH memory, EEPROM, but can also be arranged in different memory components.

The function dependent on the measured acceleration value can be a test function that measures the at least one acceleration value, in particular measures a plurality of acceleration values at time intervals, and evaluates the acceleration values. In order to evaluate the at least one acceleration value, the fluid transfer apparatus, and/or respectively, the control device preferably comprises an electrical evaluation device. The evaluation device is, in particular, a means for implementing said function, in particular the test function. The evaluation device can comprise e.g. electrical circuits which are configured for carrying out the function and which e.g. evaluate an analogue or digital signal representing the acceleration value and e.g. compare it with a reference signal or reference value by means of a comparator circuit. Particularly in the case of an acceleration value present in digital fashion, the evaluation device can comprise a digital signal processing system.

Preferably, the control device comprises at least one program data memory in which a program code can be stored. The program code is preferably designed to use the at least one acceleration value and to evaluate the latter in particular in accordance with one of the methods presented above and below. The program code is preferably a means for realizing a test function of the fluid transfer apparatus, wherein said test function uses, in particular, the at least one acceleration value and evaluates the latter in particular in accordance with one of the methods presented above and below. In this case, the program code can provide for accessing an acceleration value memory or some other data memory. The program code is preferably designed to realize the test function in the fluid transfer apparatus according to the invention. The program code can preferably be provided on a data storage medium according to the invention, in particular in order to be transferred from there to the control device or a program data memory of a fluid transfer apparatus according to the invention.

Preferably, the control device is designed to store the at least one acceleration value in particular together with a time stamp (=time data with information about a relative or absolute point in time, in particular the point in time of measurement). In this way, a test function is made possible in which the point in time of the measurement of at least one acceleration value is detected, is stored and is evaluated. This makes it possible, for example, subsequently to obtain information about the point in time of a mechanical loading or overloading of the fluid transfer apparatus, in order e.g. to be able to make the statement that the expected reliability of the fluid transfer apparatus was not adversely affected up to this point in time and the reliability should be estimated to be lower starting from this point in time. In the extreme case, it is possible to reject work processes carried out starting from this point in time of loading and/or overloading with the fluid transfer apparatus determined as "unreliable". Such a test function increases safety when using the fluid transfer apparatus.

Preferably, the control device is designed to store a multiplicity of acceleration values, in particular to store them successively at time intervals, which can be equidistant, in particular to store them continuously, or else at irregular time intervals, and/or to store them with a time stamp. In this way, in one configuration of the test function, a mechanical loading series of the fluid transfer apparatus can be recorded, which can provide information about a plurality of mechanical loadings of the fluid transfer apparatus, in particular can enable a statistical evaluation of the loading, in order to determine e.g. the sum of the loadings, the average value, the variance, in each case in particular depending on time. The evaluation can be effected "onboard" in the fluid transfer apparatus or control device or "offboard", by the data being evaluated outside the fluid transfer apparatus.

A loading history can be recorded by the fluid transfer apparatus or control device in order to realize a test function, said history making it possible to draw conclusions about the reliability of the fluid transfer apparatus. The loading history can comprise at least one dataset comprising at least one acceleration value measured by the sensor device and preferably at least one time stamp of the at least one point in time of measurement. The control device can be designed to make the loading history available via a data input/output interface in a line-conducted manner or wirelessly, and can generate or make available a loading log containing at least one acceleration value, in particular the maximum acceleration value, or containing the multiplicity of acceleration values. Furthermore, the loading log can include the at least one time stamp of the at least one acceleration value. The loading log can furthermore contain indications concerning the type of fluid transfer apparatus, an instrument serial number, and other data stored in the control device, e.g. the points in time of instrument delivery, last maintenance, or other values making it possible to draw conclusions about the reliability of the fluid transfer apparatus. Safety when using the fluid transfer apparatus is increased further in this way.

A further aspect of a test function provides for an indication signal to be output by the fluid transfer apparatus depending on the at least one measured acceleration value, which signal can be output by means of an output device of the fluid transfer apparatus, e.g. either optically by means of a display device of the fluid transfer apparatus or a loudspeaker of the fluid transfer apparatus. The control device or the evaluation device can be designed to compare the at least one acceleration value with a reference value, and in particular to output an indication signal depending on the result of this comparison. This comparison can be carried out at predetermined time intervals, in particular at equidistant time intervals, continually and repeatedly. That can take place, in particular, when a predetermined reference value is underrun, reached and/or exceeded.

The control device and/or the evaluation device and/or the acceleration sensor can be designed to compare the at least one acceleration value with a reference value, and in particular to save the result data of this comparison, referred to as "comparison data", in the acceleration value memory and/or in the dataset of a loading history. As described before, the comparison can be carried out at predetermined time intervals, in particular at equidistant time intervals, continually and repeatedly. The comparison data can contain information, if the reference value was underrun, and/or overrun, and/or reached; the comparison data can also include a time stamp or time information on when the comparison was made and/or for which period the comparison was made, for example to indicate how long the reference value was reached or underrun or overrun. In case that the comparison operation is performed at least in part by the acceleration sensor itself, the sensor evaluates the measurements; therefore the acceleration sensor becomes a part of the evaluation device of the control device of the fluid transfer apparatus. Therefore, the test function can also be executed at least in part by the electrical circuits of the acceleration sensor.

Preferably, the fluid transfer apparatus comprises an output device for outputting an indication signal for the user, wherein, in particular, the test function provides for an indication signal to be output if the at least one acceleration value preferably exceeds or, alternatively, falls below a predetermined reference value, depending on the direction of the acceleration or independently of the direction of the acceleration. The indication signal can also be output after evaluating more than one comparison value, in particular using comparison data of more than one comparison. The indication signal can be output after a predetermined condition is met. Such a condition can be, for example, that more than one comparison value, in particular a predetermined number of comparison values, in particular within a predetermined period, shows that a reference value was underrun, overrun and/or reached.

One reference value or a plurality of reference values can be stored in a reference value data memory of the fluid transfer apparatus, which memory can be associated to the control device. Provision can be made for the user to select the reference value from a plurality of proposed reference values and to set it as a predetermined reference value, or for the user to input the predetermined reference value via a user interface, e.g. operating element, wherein this input reference value is then preferably stored in the reference value data memory.

A reference value can also be defined from outside the fluid transfer apparatus automatically via a data interface of the fluid transfer apparatus. Said data interface can be wireless, e.g. on the basis of radiowaves or RFID, or on the basis of radiowaves in the ISM band or other bands, or can be wired. A reference value is preferably predetermined by the factory or determined by the user. Preferably, the control device is designed for carrying out a program for experimentally determining a reference value. In the case of this program, the user carries out at least one movement of the fluid transfer apparatus, from which a reference value is automatically derived. Preferably, the user carries out a plurality of movements of the fluid transfer apparatuses, by means of which said user wants to define the reference value, and from which a reference value is automatically derived, e.g. by averaging of a plurality of detected acceleration values.

The predetermined reference value can also be determined automatically by the control device, in particular on the basis of one or more criteria, e.g. depending on identification information of the fluid transfer apparatus, in particular an instrument serial number. By means of the indication signal, the user can be made aware of specific accelerations or loadings, in particular overloadings of the fluid transfer apparatus, whereby the reliability of the use of the fluid transfer apparatus is increased. By way of example, it may happen that a plurality of users use the fluid transfer apparatus. A second user can then be made aware of a possible unreliability of the fluid transfer apparatus, which may have occurred during the use of the fluid transfer apparatus by a first user in the case of an overloading, e.g. on account of a fall. The second user can then initiate maintenance of the instrument.

The reference value for characterizing a fall or any other motion of the fluid transfer apparatus is chosen, preferably independently of the direction of the acceleration, preferably also depending on the direction of the acceleration, from the acceleration range having the lower limit (LL) of between preferably LL=0 mg and LL=350 mg and the upper limit (UL) of between UL=350 mg and UL=2000 mg or UL=1000 mg, or preferably LL=150 mg and LL=350 mg and the upper limit (UL) of between UL=350 mg and UL=900 mg. The reference value is preferably between 200 mg and 700 mg, preferably between 220 mg and 650 mg, preferably between 240 mg and 550 mg. "g" is 9.8 m/(s*s), "mg" is 0.0098 m/(s*s). Particularly in the case of such reference values, acceleration sensors having a measurement range of (+/−) 2 g are preferably used. Values of acceleration in the range of smaller than 1 g can in particular indicate a free fall of the sensor, and therefore a free fall of the fluid transfer apparatus. During a free fall, gravity is acting on the sensor and the apparatus, respectively, in the vertical direction, substantially without any counter force, which acts in the opposite vertical direction. However, the sensor may still measure a small acceleration in the direction of gravity during free fall, which may be associated with the counter force, which is generated by the air resistance.

A fall of the sensor and the apparatus, respectively, can be detected, for example, by detecting the free fall of the sensor and/or by detecting the shock, when the apparatus hits the ground. The test function can be adapted, to measure the free fall, or alternatively, the shock, in order to detect a fall. Moreover, the test function can be adapted to measure the free fall and the shock, i.e. to measure both events.

The event of a shock can be detected, for example, by determining if the acceleration value exceeds or reaches or underruns a predetermined reference value. A shock usually is characterized by high-g values, which act on the sensor during an abrupt deceleration of the sensor after a free fall. A shock can be characterised by a multiple of g: using the acceleration sensor, the shock will cause the sensor to be in "overload" status during the impact. Therefore, it is typical to detect the maximum possible absolute values of acceleration, which can be measured, when an apparatus with the acceleration sensor hits the ground. For example, an acceleration sensor, which is adapted to measure in a predefined range of LL (lower limit e.g. −2 or −4 g) and UL (upper limit, e.g. 2 or 4 g), can measure the acceleration value of LL, e.g. −2 or −4 g or UL, 2 or 4 g, during the shock event. Preferably, the test function is adapted to detect a lower limit or upper limit for the acceleration value, e.g. +/−2 g or +/−4 g, in order to detect a shock. Such a value can correspond to the range limits (LL or UL), which determine the physical capacity of the acceleration sensor to measure acceleration.

A shock can also be characterized by the acceleration value, which typically occurs during the short bouncing period, which takes place immediately after the impact. An object, which hits the ground, usually bounces back from the ground due to the elasticity of the object and/or the ground. During a bouncing period, low-g acceleration values can be measured. Preferably, the test function is adapted to detect an acceleration value, which can be the absolute value, of between 0.0 mg and 150.0 mg, or between 0.0 mg and 125.0 mg in order to detect a shock.

It is further possible and preferred that the test function is adapted to measure the time period during which the comparison of the acceleration values, being subsequently measured, and the reference value has a certain result, for example, that the acceleration values exceed the reference value during said period, or that the acceleration values underrun the reference value during said period or that the acceleration values equal the reference value during said period. It is preferred that the fluid transfer apparatus, and/or the acceleration sensor and/or the control device perform the measurement of acceleration repeatedly, in particular by a frequency f of subsequent measurements, wherein preferably 10 Hz<=f<=100 Hz, preferably 15 Hz<=f<=50 Hz.

Moreover, the test function can be adapted to measure the free fall and the shock, i.e. to measure both events, by detecting a characteristic sequence of acceleration values, which corresponds to a combined motion of a free fall and a shock. Preferably, a first dataset of multiple acceleration values are measured, which characterise a free fall, and second, a second dataset of multiple acceleration values are measured, which characterise a shock. The values of the first and second dataset are at least in part different. The second dataset can contain high-g acceleration values and/or low-g acceleration values, which correspond to an impact and a bouncing, respectively. It is possible an preferred that the algebraic signs of the acceleration values in the second dataset are, preferably at least in part, opposite to the algebraic signs of the acceleration values in the first dataset. This means, the direction of accelerations being measured are opposite during free fall and during the bouncing-back of the fluid transfer apparatus. Such a characteristic sequence more reliably indicates a shock event, having acted on the apparatus.

It is preferred that the evaluation device and/or the test function are adapted to analyse the measured acceleration values, in order to determine a characteristic pattern in the acceleration values, which indicate a free fall and/or a shock event, or another event to be detected. Such an analysis can also provide to perform at least one statistical method on the data, e.g. calculating the mean and/or the standard deviation of at least a part of the values or of substantially all values. Such an analysis can also provide to compare the data, which contain multiple acceleration values, with reference data, which also contain multiple acceleration values (reference values). Using such a characteristic pattern of acceleration data can more reliably indicate a certain event, e.g. a free fall and/or a shock event, having acted on the apparatus.

A test function can also provide for the at least one acceleration value to be used for activating or implementing a second function of the instrument. The second function is preferably implemented depending on the at least one acceleration value. Said second function can be e.g. transferring the fluid transfer apparatus from a first operating state to a second operating state. An operating state of the fluid transfer apparatus may be characterized by a specific value of the power consumption or of the work electrically performed by an electrical device of the fluid transfer apparatus. Preferably, the first operating state is a standby state of the fluid transfer apparatus, in which the electrically controlled functions of the fluid transfer apparatus are temporarily deactivated, and the second operating state is preferably a useful state in which at least one of the functions deactivated in the first state is activated and, in particular, the fluid transfer apparatus is used as intended. What can be achieved by means of such a test function is, in particular, that the second function is automatically implemented by automatic evaluation of the at least one acceleration value, such that starting the second function does not require a dedicated operating element or such an operating function that requires deliberate user intervention. Such an operation would also be a mechanical actuation of the fluid transfer apparatus, which might likewise lead to wear and to an unreliable function of the fluid transfer apparatus. The automatic implementation of the second function therefore improves the reliability of the use of the fluid transfer apparatus. Furthermore, the standby duration or lifetime of a battery or of a rechargeable battery can be improved by means of such a test function.

Preferably, the control device and/or the evaluation device are/is designed to compare the acceleration value with a predetermined reference value, and in particular to implement the second function depending on the result of a comparison of the at least one acceleration value with at least one reference value, namely to start or not to start it, or to start it in modified fashion, i.e. with one or more parameters being transferred to the second function, wherein said parameter can include the acceleration value or e.g. a time value. Said comparison can be carried out at predetermined time intervals, in particular at equidistant time intervals, continually and repeatedly and, in particular, automatically, i.e. in particular without user action. The second function can be implemented differently in a time-dependent manner, for example, such that e.g. a fluid transfer apparatus can be switched on (activated into the useful state) or switched off (electrical functions are deactivated) in a time-dependent manner. The reference value can be defined according to one of the methods described above or below for determining the predetermined reference value.

The reference value for transferring the fluid transfer apparatus from a standby state to a useful state is chosen, preferably independently of the direction of the acceleration, preferably also depending on the direction of the acceleration, from the acceleration range having the lower limit (LL) of between LL=1 mg and LL=150 mg and the upper limit (UL) of between UL=200 mg and UL=500 mg. The reference value is preferably between 0 mg and 400 mg, preferably between 150 mg and 350 mg, preferably between 200 mg and 350 mg, preferably between 220 mg and 320 mg. "g" is 9.8 m/(s*s), "mg" is 0.0098 m/(s*s). Particularly in the case of such reference values, acceleration sensors having a measurement range of (+/−) 2 g preferably used.

In the present case, a fluid transfer apparatus or a control device designed for embodying a specific function, in particular test function, is understood to mean such a fluid transfer device or control device which is not only suitable in principle for carrying out said function, e.g. after running software, but rather already has all means for actually fulfilling said function, e.g. by already having the necessary program code or the necessary software, in particular in the form of firmware of the fluid transfer apparatus.

The means for implementing said function or test function comprise, in particular, an evaluation device.

The invention furthermore relates to a method for using at least one acceleration value measured by a fluid transfer apparatus according to the invention in said fluid transfer apparatus, wherein the method provides, in particular, for evaluating the at least one acceleration value, in particular for comparing it with at least one reference value, or for carrying out all of the test functions described above or other steps mentioned above in the description of the various test functions.

Further preferred configurations of the apparatus according to the invention and of the method according to the invention will become apparent from the following description of the exemplary embodiments in association with the figures.

Figure 1:
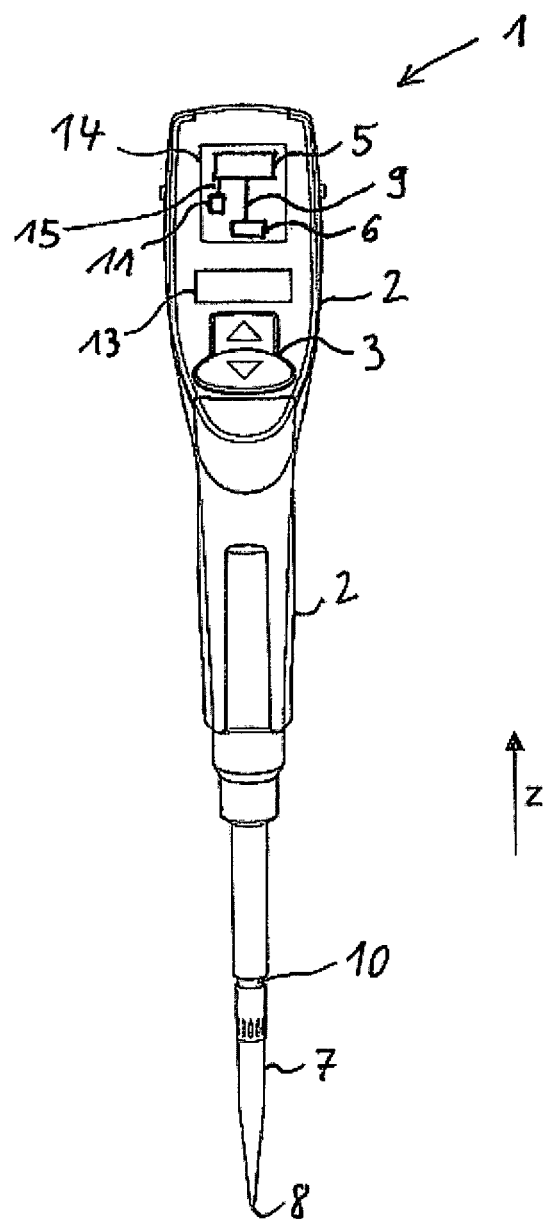
FIG. 1 shows an exemplary embodiment of the fluid transfer apparatus according to the invention, said apparatus here being an electrical piston stroke pipette.

The electrical piston stroke pipette 1 in FIG. 1 comprises a base body having the housing 2. The housing 2 is embodied as a handle and for operating the pipette 1 with one hand, such that the user e.g. with the other hand can fix sample containers (not shown) between which the user transfers a liquid by means of the pipette 1, e.g. a biochemical laboratory sample in a predominantly water-containing solvent (aqueous sample) or a medical laboratory sample. For this purpose, the user starts the intake or the delivery of the sample by means of the central actuating button 3 of the pipette. The actuating button 3 is a rocker switch having a neutral position and an "intake" and a "delivery" position. The pipette contains a cylinder and a piston, which is movable in an air-tight manner in said cylinder and between the lower end of which and a sample liquid arranged in the pipette tip 7 an air cushion is situated. The pipette furthermore contains an electrically driven movement device, by means of which the piston can be moved. In the case of a movement upward (in the positive z-direction) the air cushion expands, as a result of which the liquid can be taken in through the opening 8 into the pipette tip 7, and, in the case of a movement downward, the air cushion is compressed, as a result of which the liquid can be delivered from the pipette tip 7 to the opening 8. Very small quantities of liquid can be metered depending on the type of pipette and of pipette tips used therewith. The highest possible precision is desired. The pipette tip 7 is connected to the pipette at the connection section 10 of the pipette.

Figure 2:
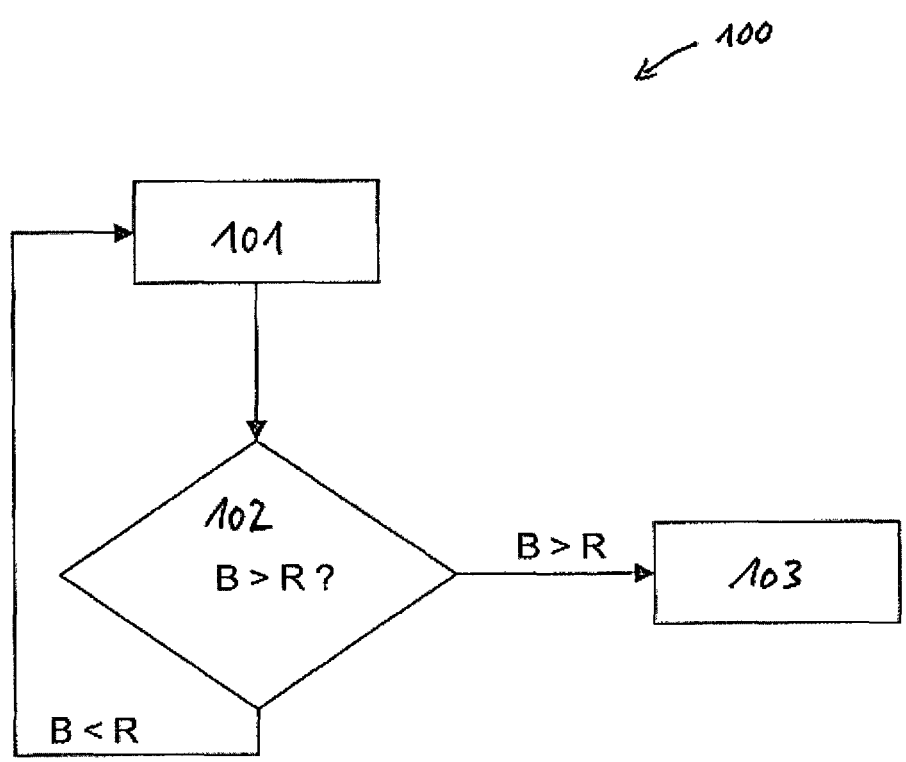
FIG. 2 shows an exemplary embodiment of part of the method according to the invention in which an acceleration value is evaluated in the fluid transfer apparatus in FIG. 1.

The pipette 1 comprises a control device 5, which is accommodated in the form of electrical integrated circuits at least partly on a printed circuit board 14. The acceleration sensor 6 of the sensor device of the pipette is arranged on the same printed circuit board, said acceleration sensor being operated by the same voltage supply as the control device and the pipette 1. The pipette 1 furthermore comprises a timer 11, which is signal-connected to the control device 5 via the line 15 and is fed by a separate battery. The acceleration sensor 6 is signal-connected to the control device 5 via the electrical line 9, such that electrical signals can be transmitted between sensor device and control device in a line-conducted manner. The control device 5 is designed to transfer a trigger signal to the sensor device at predetermined time intervals of e.g. 500 ms, on account of which an electrical signal is transmitted to the control device by the acceleration sensor 6. The electrical signal transports three acceleration values corresponding to the three measurements of the acceleration sensor 6, which are carried out substantially simultaneously by said acceleration sensor along orthogonal spatial axes on account of the trigger signal. This measurement is step 101 of the method 100 in FIG. 2.

The electrical control device is designed for carrying out a test function. Said test function provides for comparing the magnitude of the three-dimensional vector of the acceleration B with a reference value (step 102 in FIG. 2), and for carrying out step 103 if the acceleration B exceeds the reference value R, and otherwise for starting the measurement 101 anew. It is also possible to provide termination conditions for this continually repeated evaluation, but said conditions are not shown in FIG. 2. In particular switching off the electrical pipette preferably generally terminates the test function, in particular also the case where a specific acceleration value, which can be e.g. zero or close to zero, is not exceeded over a predetermined time period, which can preferably be set by the user.

Step 103 can provide for an acoustic or optical indication signal to be output to the user via the user interface 13 (FIG. 1). In this way, the user can be made aware of an overloading state of the pipette which was present at the point in time of the measurement. The acceleration value correspondingly measured and determined by evaluation can be stored as overloading value with a time stamp in a data storage device of the pipette in order to be retrieved and output later. Typical reference values for a fall of the pipette are e.g. 250 mg to 520 mg. The use of the pipette becomes more reliable by virtue of the test function, since maintenance of the instrument can be initiated in a timely manner.

Step 103 can preferably also provide for transferring the pipette from a standby state, in which some electrical functions of the pipette with relatively high power consumption are deactivated and during which said test function is carried out, to a useful state in which said electrical functions are activated and in which the pipette is completely ready for use. Typical reference values for changing the operating modes of the pipette are in this case e.g. 220 mg to 350 mg. These values correspond to the typical accelerations which occur when the pipette is picked up from a storage position on a table into the user's hand. It is provided that this reference value predetermined at the factory can be changed by the user via the user interface of the pipette, which makes the use more convenient for the user. The pipette switches automatically between the operating modes depending on the measured acceleration, such that the actuation of an operating element potentially susceptible to wear does not arise nor is a user intervention required. The pipette can be operated more conveniently in this way, wear is reduced and the use of the pipette is more reliable.

The invention claimed is:

1. A fluid transfer apparatus (1), in particular a pipetting apparatus, for transferring at least one fluid laboratory sample, in particular a biochemical or medical laboratory sample, comprising:
a handheld base body (2), which has a connecting section (10) serving for connecting a container (7) to the base body for the intake of the at least one fluid sample into the container,
a movement device, which can bring about the intake and/or delivery of at least one fluid laboratory sample into the container,
an electrical control device (5), which controls at least one function of the fluid transfer apparatus,
a sensor device, which has at least one acceleration sensor (6), which is signal-connected to the control device and by means of which at least one acceleration value can be measured during the movement of the fluid transfer apparatus,
wherein the control device is designed such that it uses the at least one acceleration value during the control of the at least one function, the fluid transfer apparatus comprising an evaluation device, which is designed for comparing the at least one measured acceleration value with at least one predetermined reference value, and wherein the fluid transfer apparatus is configured for implementing said function by means of electrical circuits and/or a program code, wherein said function is a test function programmed to use the at least one measured acceleration value, wherein the test function is programmed to provide for the fluid transfer apparatus to be put into a second operating state from a first operating state depending on the result of a comparison of the at least one measured acceleration value with the at least one reference value and wherein the first operating state is a standby state, during which at least one electrically operated function of the fluid transfer apparatus is deactivated, and the second operating state is a useful state in which said electrically operated function is activated, or wherein the fluid transfer apparatus has a reference value data memory, the at least one reference value being stored in the reference value data memory, the at least one reference value characterizing a free fall of the fluid transfer apparatus and/or a shock when the fluid transfer apparatus hits the ground after a free fall, and the test function being adapted for detecting a fall of the fluid transfer apparatus by way of comparing the at least one measured acceleration value with at least one reference value of an acceleration, and saving the result data of this comparison in an acceleration value memory of the fluid transfer apparatus.

2. The fluid transfer apparatus according to claim 1, wherein the evaluation device comprises a signal processing device.

3. The fluid transfer apparatus according to claim 1, wherein the fluid transfer apparatus has an output device for outputting an indication signal to the user, and wherein the test function furthermore provides for an indication signal to be output if the at least one acceleration value lies outside a range characterized by a predetermined reference value.

* * * * *